United States Patent [19]

Barker

[11] Patent Number: 4,950,542
[45] Date of Patent: Aug. 21, 1990

[54] ARTICLES HAVING AROMA

[76] Inventor: Robert S. Barker, 47 George St., Bloomfield, N.J. 07003

[21] Appl. No.: 307,210

[22] Filed: Feb. 3, 1989

Related U.S. Application Data

[63] Continuation of Ser. No. 857,837, Apr. 30, 1986, abandoned.

[51] Int. Cl.$^5$ .................... C08G 14/00; C08G 18/00
[52] U.S. Cl. ................... 428/403; 428/407; 428/925; 63/DIG. 2
[58] Field of Search .............. 428/905, 403, 407; 63/2, 1, DIG. 2, DIG. 1

[56] References Cited

U.S. PATENT DOCUMENTS

| | | | |
|---|---|---|---|
| 2,169,055 | 3/1937 | Overshiner | 428/905 |
| 3,303,046 | 2/1967 | Chebiniak | 428/905 |
| 3,553,296 | 1/1971 | Gaeckel | 428/905 |
| 3,578,545 | 5/1971 | Carson | 428/905 |
| 3,623,659 | 11/1971 | Maierson | 428/905 |
| 3,655,129 | 4/1972 | Seiner | 428/905 |
| 3,685,734 | 8/1972 | Paciorek | 428/905 |
| 3,688,985 | 9/1972 | Engel | 428/905 |
| 3,994,439 | 11/1976 | VanBreen | 428/905 |
| 4,095,031 | 6/1978 | Engel | 428/905 |
| 4,223,070 | 9/1980 | Hahn | 428/905 |
| 4,226,944 | 10/1980 | Stone | 428/905 |
| 4,289,832 | 9/1981 | Schwarz | 428/905 |
| 4,293,602 | 10/1981 | Coffey | 63/DIG. 2 |
| 4,617,230 | 10/1986 | Shah | 428/905 |
| 4,713,291 | 12/1987 | Sasaki | 428/905 |

FOREIGN PATENT DOCUMENTS

| | | |
|---|---|---|
| 610105 | 1/1926 | France . |
| 0684956 | 2/1929 | France . |
| 0650144 | 7/1930 | France . |

*Primary Examiner*—Robert A. Hafer
*Assistant Examiner*—Michael Brown
*Attorney, Agent, or Firm*—Bauer & Schaffer

[57] ABSTRACT

Articles are coated to provide a sustained release of aroma with a composition of a homogeneous emulsion of polyurethane and essential oils.

4 Claims, 1 Drawing Sheet

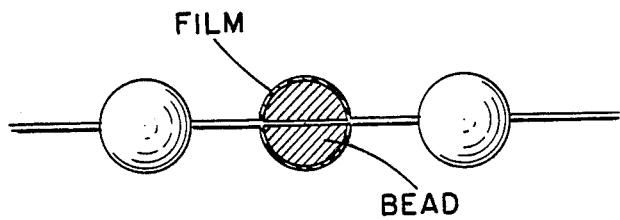

ARTICLES HAVING AROMA

This is a continuation of Ser. No. 857,837 filed Apr. 30, 1986, now abandoned.

BACKGROUND OF THE INVENTION

The present invention relates to the manufacture of articles of wear and in particular to costume jewelry, wearing apparel and sundry items capable of exuding a sustained release of fragrance.

Perfumes and fragrances have been widely used by both men and women by the direct application to their bodies and/or clothes. It would, however, be desirable to provide perfumes and pleasant odors directly on various products such as apparel jewelry, packages or sundry items on a sustained and generally lasting basis. In addition, it would be advantageous to provide such products with fragrances which correspond to their inherent characteristics or forms providing a more realistic attribute thereto.

It is the object of the present invention to provide for the manufacture of articles of intimate or near intimate use which exude fragrance and odor as an inherent part of such article.

It is a further object to provide costume jewelry, wearing apparel and sundry items having fragrances applied as a constituent thereof which neither alters, modifies or changes the appearance, surface color, or basic constituents of the material forming the article.

It is still a further object to provide a composition in which fragrances are an essential element thereof, so that it can be applied easily to any article or product in a manner to exude an aroma over a sustained period of time without changing or modifying the article or product in any way except to permit the exudation of said fragrance.

These objects as well as other objects will be recognized from the following description of the present invention.

According to the present invention articles are provided of plastic and/or natural substances, fabrics from which wearing apparel can be made, and sundry items can be fashioned so that combined with them or applied to them, is a polyurethane emulsion containing essential oils or fragrances.

In particular, the present invention provides a composition formed by the admixture under normal agitation, as with a blender or mixer, of between 3 to 33% parts per weight, of an oil fragrance in a thermally oxidated stabilized polyurethane comprising a hydrazine treated NCO terminated anionic prepolymer, until such mixture is homogeneous. Thereafter, the mixture can be applied as a film to a preformed costume jewelry, wearing apparel and sundry item or the costume jewelry, wearing apparel, and sundry can be soaked or dipped in the mixture. Finally, the article to which the mixture is applied is dried.

The mixture of the present invention is clear and colorless, is without harm to the article or the material it is made of, and has a sustained release of fragrance over an extended period of time.

An extremely suitable polyurethane is that commercially available system known as WITCOBOND 232 supplied by the WITCO Chemical Company in New York. Such a system is of the type disclosed in U.S. Pat. No. 4,447,571. Another suitable system is found in U.S. Pat. No. 3,873,484.

Conventional oil based fragrances and odors in the form of essential oils, of any type may be used. When the polyurethane and essential oils are mixed under light activation, the oils are surprisingly solubilized having a particle size in the dispersed phase of oil of about .1–1.0 mu, in a clear homogeneous emulsion. In general, a lattice or dispersion having an average particle size less than .5 $\mu$u is obtained. Under microscopic examination, the essential oils are uniformly dispersed throughout the matrix of the polyurethane dispersion.

The essential oil may be mixed with the polymer directly, although it may be preferred to insure a homogeneous emulsion that a surfactant be used.

Surprisingly, the mixture with this particular system is clear and adheres well to any substrate whether applied by film or bath and subsequently the fragrances in the clear film are released slowly over a period of 30 days to 180 days depending on the level of the essential oil and on the thickness of the final coating. A final coating of 0.5 to 10 mil. thickness being the most desirable.

The essential oils can be added at once or incremental levels to the polyurethane, again depending on the oil. The final mixture or emulsion has an indefinite shelf life remaining fluid for dipping, spraying, or other physical means of deposition over a long period of time.

Surprisingly, the film or coating even after drying is clear and shows no indication of any entrapped oil or fragrance. It is even more surprising that the resultant mixture of the polyurethane and essential oils is a homogeneous emulsion having very small uniform particles within the range of .1–1.0 $\mu$u with the majority of such particles at approximately 1.0 $\mu$u. This result is largely unexpected in view of the fact that polyurethane is a basically aqueous system while the essential oil is a basically non-soluble, in water, system. In large measure it has been found that the essential oils are in fact soluble in the polyurethane system under the light agitation of the mixing step. For this reason, coatings may be applied by spraying, dipping or otherwise, in layers of 1 to 5 mil. thick.

The resultant emulsion differs considerably from known systems in which fragrances have been sought to be encapsulated within polyurethane beads or the like. In the prior systems essential oils were not employed, but instead the fragrances encapsulated were alcohol or other ester based systems in which the essential oil had already been captured by a solvent.

A typical application could be the application of such a film on decorative jewelry such as earrings, necklaces, etc. In addition, the films can be applied to certain cosmetic packages to demonstrate fragrances contained in the container. Films by dipping or spraying can be applied to certain porous substrates to yield deodorizers, long-lasting scented or artificial flowers, etc.

EXAMPLE I

Preparation of composition:

10 grams of essential oil Rose Natural #629 (manufactured by Felton International, Brooklyn, N.Y.) was added slowly to 90 grams of WITCOBOND 232 and mixed under normal mechanical agitation in an electric laboratory stirrer for about 30 seconds until a homogenous mixture was observed. The resultant mixture was observed under the microscope. The mixture surprisingly contained solubilized fragrance oils uniformly dispersed in the polyurethane and was a clear translucent fluid of low viscosity.

Preparation of article:

Strands of pearl necklaces of varying length are dipped into the prepared emulsion composition and then allowed to air dry. The pearls had a coating of 0.5–1 M thickness which was clear and colorless as well as dry and smooth to the touch. The coating in no way altered the original color, gloss or appearance of the pearl necklace. The necklace exuded the odor of the original essential oil lasting at least 3 months, without manipulation, rubbing or subsequent heating.

Several additional strands of cultured and plastic pearly necklaces were dipped in the emulsion, some air dried, and others were dried in a laboratory and/or under a heat blower for rapid drying. The mode of drying is not critical and cool air or hot air may be used. All of the coated beads has the same surprising and advantageous results noted.

The essential oils, fragrances, or odors mentioned heretofore are employed in each of the following examples:

As a comparative set of examples, a composition of 10 percent Rose Natural #629 oil was prepared and test strands were coated and dried as above. The strands showed complete disappearance of fragrance in less than four (4) days.

EXAMPLE II

To 90 pts of obsession type frangrance #244 (manufactured by Felton International, Brooklyn, New York) 10 pts. of a surfactant (Triton X100, manufactured by Rohm and Haas, Philadelphia, PA) was added and mixed as in Example I. This mixture was then added to the polymer latex with high speed mixing while avoiding excessive air entrainment. The additions are made slowly in small increments. The final product is a pink, translucent system indicating a submicron particle size of the polymer/surfactant/fragrance blend, exhibiting the same characteristic as found in Example I. The resultant articles coated with this composition also exuded fragrance for over three months.

EXAMPLE III A - III D

The blends of fragrances listed in the following table, derived from Cosmetics - Science and Technology, E. Sagarin, Interscience Publishers, 1957, were each mixed with the polymers, in accord with each of Examples I and II. In each instance, similar results in both the mixture and in the ultimate coating was obtained.

TABLE

|  | (A) Lilac | (B) Rose | (C) Muguet | (D) Jasmin |
| --- | --- | --- | --- | --- |
| Phenyl ethyl alcohol | 30% | 35% | 15% | 05% |
| Hydroxycitronellal | 30 | — | 45 | 06 |
| Geraniol | 02 | 48 | 20 | 02 |
| Amyl cinnamic aldehyde | 04 | 02 | 05 | 45 |
| Benzyl acetate | 05 | 04 | 05 | 40 |
| Ionone | 03 | 04 | 05 | — |
| Eugenol | 01 | 02 | — | — |
| Terpineol | 25 | 05 | 05 | 02 |

EXAMPLE IV

A composition was formed according to Example I mixing 97 grams of WITCOBOND 232 (a polyurethane latex, Wito Chemical Corp., NY) with 3 grams of an essential oil, and several strand articles, such as plastic pearls, rhinestone jewelry, plastic flowers, etc. were coated to thicknesses between 1 and 5 mil. by spray and/or dipping; the resultant article dried. The resultant article exuded fragrance for about 4 weeks.

EXAMPLE V

A composition was formed according to Example I mixing 95 grams of WITCOBOND 240 (polyurethane latex) with 20 grams of an essential oil and several articles coated as in the preceding example. The resultant article exuded fragrance for about eight weeks.

EXAMPLE VI

A composition was formed according to Example I mixing 90 grams of the polyurethane with 7 grams of an essential oil and 3 grams of Triton X-100, a surfactant (manufactured by Rohm and Haas, Phil., PA) several articles were coated as in the preceding example. The resultant article exuded fragrance for about 12 weeks.

EXAMPLE VII

A composition was formed according to Example I mixing 80 grams of the polyurethane with 15 grams of an essential oil and 5 grams of Triton X-100 (manufactured by Rohm & Haas) several articles coated as in the preceding example. The resultant article exuded fragrance for about 18 weeks.

These and other objects of the invention will be apparent to those skilled in the art. It is, therefore, intended that the scope of the invention should not be limited by the description, but only by the claims appended hereto.

What is claimed is:

1. A method of forming a coating composition for the sustained release of an essential oil fragrance, which comprises the steps of admixing 3 to 20 parts by weight of an essential oil and 97 to 80 parts by weight of an aqueous polyurethane latex; and mechanically agitating the admixture until a clear homogeneous colloidal dispersion is formed having a particle size between 0.1 and 1.0 micron and thereafter forming said dispersion into a clear cohesive film capable of sustained release of the essential oil fragrance.

2. The method according to claim 1 in which a surfactant is added to the admixture.

3. An article containing a coating made in accordance with the method of claim 2.

4. An article containing a coating made in accordance with the method of claim 1.

* * * * *